(12) United States Patent
Nomura

(10) Patent No.: US 10,058,857 B2
(45) Date of Patent: Aug. 28, 2018

(54) METHOD FOR PREPARING CATALYST

(71) Applicant: Kao Corporation, Tokyo (JP)

(72) Inventor: Yukiko Nomura, Wakayama (JP)

(73) Assignee: KAO CORPORATION, Tokyo (JP)

( * ) Notice: Subject to any disclaimer, the term of this patent is extended or adjusted under 35 U.S.C. 154(b) by 0 days.

(21) Appl. No.: 15/532,929

(22) PCT Filed: Dec. 16, 2015

(86) PCT No.: PCT/JP2015/085175
§ 371 (c)(1),
(2) Date: Jun. 2, 2017

(87) PCT Pub. No.: WO2016/098801
PCT Pub. Date: Jun. 23, 2016

(65) Prior Publication Data
US 2017/0341070 A1    Nov. 30, 2017

(30) Foreign Application Priority Data

Dec. 18, 2014 (JP) ................................ 2014-255846

(51) Int. Cl.
| | |
|---|---|
| C07C 69/66 | (2006.01) |
| B01J 37/04 | (2006.01) |
| B01J 37/18 | (2006.01) |
| B01J 23/644 | (2006.01) |
| B01J 37/02 | (2006.01) |
| C07C 51/235 | (2006.01) |
| C07C 59/125 | (2006.01) |
| B01J 37/03 | (2006.01) |
| B01J 21/18 | (2006.01) |
| B01J 35/00 | (2006.01) |
| B01J 37/00 | (2006.01) |
| C07B 61/00 | (2006.01) |

(52) U.S. Cl.
CPC .............. *B01J 37/04* (2013.01); *B01J 21/18* (2013.01); *B01J 23/644* (2013.01); *B01J 23/6447* (2013.01); *B01J 35/002* (2013.01); *B01J 35/0013* (2013.01); *B01J 37/009* (2013.01); *B01J 37/02* (2013.01); *B01J 37/031* (2013.01); *B01J 37/18* (2013.01); *C07C 51/235* (2013.01); *C07C 59/125* (2013.01); *C07B 61/00* (2013.01)

(58) Field of Classification Search
CPC ........ B01J 37/04; B01J 23/6447; B01J 37/18; B01J 23/644; B01J 37/02; C07C 51/235; C07C 59/125; C07B 61/00
See application file for complete search history.

(56) References Cited

U.S. PATENT DOCUMENTS

| | | | |
|---|---|---|---|
| 4,845,208 A | 7/1989 | Fuertes et al. | |
| 5,132,452 A | 7/1992 | Deller et al. | |
| 5,756,853 A | 5/1998 | Metivier et al. | |
| 2007/0100161 A1 | 5/2007 | Ebner et al. | |
| 2012/0296115 A1 | 11/2012 | Shirasawa et al. | |
| 2014/0088323 A1 | 3/2014 | Sakaguchi | |

FOREIGN PATENT DOCUMENTS

| | | | |
|---|---|---|---|
| JP | 62-228093 A | | 10/1987 |
| JP | 2-72137 A | | 3/1990 |
| JP | 4-305538 A | | 10/1992 |
| JP | 7-173099 A | | 7/1995 |
| JP | 9-512286 A | | 12/1997 |
| JP | 10-158227 A | | 6/1998 |
| JP | 11-279110 | * | 10/1999 |
| JP | 11-279110 A | | 10/1999 |
| JP | 2002-504427 A | | 2/2002 |
| JP | 2012-595 A | | 1/2012 |
| WO | WO 2012/169585 A1 | | 12/2012 |

OTHER PUBLICATIONS

US 6,337,298, 01/2002, Ebner et al. (withdrawn)
JP11-279110 translated 1999 (Year: 1999).*
Keresszegi et al., "A simple discrimination of the promoter effect in alcohol oxidation and dehydrogenation over platinum and palladium," Journal of Catalysis, vol. 225, 2004 (Available online May 12, 2004), pp. 138-146.
Machine translation of JP-11-279110-A published on Oct. 12, 1999.
Machine translation of JP-7-173099-A published on Jul. 11, 1995.
Machine translation of JP-4-305538-A published on Oct. 28, 1992.
Machine translation of JP-10-158227-A published on Jun. 16, 1998.
International Search Report issued in PCT/JP2015/085175 (PCT/ISA/210), dated Feb. 2, 2016.
International Preliminary Report on Patentability and English translation of the Written Opinion of the International Searching Authority (Forms PCT/IB/373 and PCT/ISA/237) dated Jun. 20, 2017, for International Application No. PCT/JP2015/085175.
Extended European Search Report for European Application No. 15870003.9, dated Jun. 26, 2018.

* cited by examiner

*Primary Examiner* — Yevgeny Valenrod
*Assistant Examiner* — Blaine G Doletski
(74) *Attorney, Agent, or Firm* — Birch, Stewart, Kolasch & Birch, LLP

(57) ABSTRACT

[Problem to be Solved]
To provide a method for preparing a catalyst that has high activity and exhibits high durability with reduced elution of a catalyst metal when a liquid-phase oxidation reaction is brought about without combined use of an alkali; and a method for producing an oxide highly efficiently by use of the catalyst.
The method for preparing a catalyst has the following Steps 1, 2 and 3.
Step 1: preparing an aqueous dispersion of a catalyst carrying Pt on activated carbon;
Step 2: preparing an aqueous solution containing Bi in an ionic state; and
Step 3: adding the aqueous dispersion obtained in Step 1 to the aqueous solution obtained in Step 2.

16 Claims, 1 Drawing Sheet

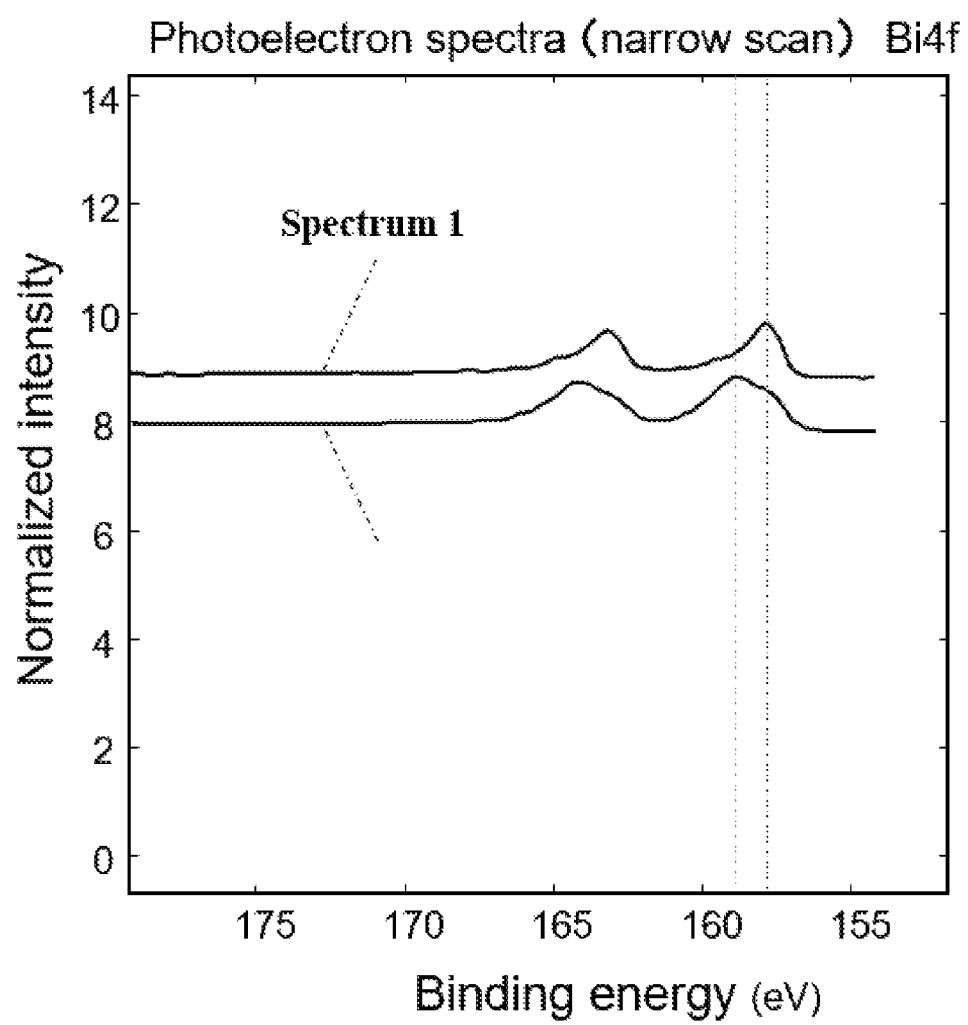

METHOD FOR PREPARING CATALYST

TECHNICAL FIELD

The present invention relates to methods for preparing a catalyst. More specifically, the present invention relates to a method for preparing an oxidation reaction catalyst, which can be suitably used in producing a carboxyl compound or a ketone compound by oxidizing a hydroxy compound such as an alcohol and polyoxyalkylene alkyl ether, or an aldehyde compound.

BACKGROUND ART

Conventionally, known is a method, which uses Pt as a noble metal catalyst in combination with Bi as a promoter, causes catalytic oxidation on a hydroxy compound or an aldehyde compound and converts to a corresponding carboxyl compound or ketone compound. For example, JP-A 11-279110 discloses a method for producing 2-substituted-3-hydroxypropionic acids or 2-substituted malonic acids by: preparing a catalyst carrying Bi by adding dropwise a nitric acid aqueous solution of bismuth nitrate salt to a commercially available Pt/C catalyst dispersion; and using the catalyst for catalytic oxidation of 2-substituted-1,3-propanediol with an oxygen-containing gas. Further, Journal of Catalysis 225 (2004) (pages 138 to 146) discloses a method, which includes preparing a catalyst carrying Bi by adding dropwise an acetic acid aqueous solution of bismuth nitrate salt to $Pt/Al_2O_3$ and using the catalyst for liquid-phase oxidation of 1-phenylethanol, 2-octanol and cynnamyl alcohol. JP-A 62-228093 describes that, in a reaction for obtaining gluconate from glucose, Pd/C is used as a catalyst and Bi is carried as a promoter. Bi is carried by mixing a promoter solution with a Pd/C suspension. Herein, Pt denotes platinum, Bi denotes bismuth, Pd denotes palladium and C denotes activated carbon.

SUMMARY OF THE INVENTION

When a conventional Pt—Bi/C catalyst is used for oxidation reaction, a reaction proceeds smoothly from an early stage to a middle stage, but observed is a phenomenon where a reaction rate significantly decreases especially at the last stage of the reaction or the reaction stops without completion thereof. Further, observed is a phenomenon where a carried metal is eluted from a catalyst into a solution after a reaction thereby to deteriorate the durability. These phenomena are generally observed in oxidation reaction using a noble metal catalyst carrying Bi though they differ in degree depending on the structure of a matter to be oxidized.

JP-A 11-279110 describes that, in a reaction for obtaining 2-substituted-3-hydroxypropionic acid and 2-alkylmalonic acid from 2-substituted-1,3-propanediol, not only a Pt—Bi/C catalyst carrying Bi as a second metal component, but also a Pt—Pd/C catalyst or a Pt—Pb/C catalyst carrying Pd or Pb, respectively, may be used. However, use of them results in a low yield. Further, in all of the reactions described in JP-A 11-279110, it is necessary to add an alkali in addition to a catalyst to enhance the selectivity.

Further, JP-A 62-228093 describes that when Bi is carried on Pd/C, it exhibits higher activity than the case where Pd is carried on Bi/C. However, this fails to provide a finding that sufficiently addresses the above problem, and also requires combined use of a catalyst and an alkali for reaction, like the case described in JP-A 11-279110.

Furthermore, in Journal of Catalysis 225 (2004) (pages 138 to 146), for liquid-phase oxidation of a compound having a hydroxyl group, a $Pt—Bi/Al_2O_3$ catalyst is used as described above. However, it is not satisfactory in terms of both the activity and the metal elution if a reaction is brought about without combined use of an alkali.

An object of the present invention is to provide a method for preparing a catalyst that has high activity and exhibits excellent durability with reduced elution of a catalyst metal when a liquid-phase oxidation reaction is brought about without combined use of an alkali.

The present inventor has continuously made researches on a method for preparing a Pt—Bi/C catalyst in order to solve the above-described problem of a Pt—Bi/C catalyst in a liquid-phase oxidation reaction as described above, resulting in the completion the present invention.

The present invention is a method for preparing a catalyst, which has the following Steps 1, 2 and 3.

Step 1: preparing an aqueous dispersion of a catalyst carrying Pt on activated carbon;

Step 2: preparing an aqueous solution containing Bi in an ionic state; and

Step 3: adding the aqueous dispersion obtained in Step 1 to the aqueous solution obtained in Step 2.

According to the present invention, there is obtained a catalyst that has high activity and exhibits excellent durability with reduced elution of a catalyst metal when a liquid-phase oxidation reaction is brought about without combined use of an alkali. Further, there is provided a method for producing an oxide in a highly efficient manner by use of such catalyst.

BRIEF DESCRIPTION OF THE DRAWING

The FIGURE shows photoelectron spectra of Bi4f orbitals, in which a spectrum 1 indicates a result obtained by making measurement in Example 7 on a catalyst prepared in Example 1; and a spectrum 2 indicates a result obtained by making measurement in Comparative Example 3 on a catalyst prepared in Comparative Example 1.

DESCRIPTION OF EMBODIMENTS

The present invention is a method for preparing a catalyst that has the following Steps 1, 2 and 3.

Step 1: preparing an aqueous dispersion of a catalyst carrying Pt on activated carbon;

Step 2: preparing an aqueous solution containing Bi in an ionic state; and

Step 3: adding the aqueous dispersion obtained in Step 1 to the aqueous solution obtained in Step 2.

The aqueous dispersion of catalyst carrying Pt on activated carbon prepared in Step 1 is added to the aqueous solution containing Bi in an ionic state prepared in Step 2, and this enables preparation of a catalyst that has high activity and exhibits excellent durability with reduced elution of a catalyst metal when a liquid-phase oxidation reaction is brought about without combined use of an alkali. The reason therefor is not clear, but it is considered as follows. When an aqueous dispersion of catalysts carrying Pt on activated carbon is added to an aqueous solution containing Bi ions, Bi ions are brought into contact with Pt more evenly in comparison with a case where Pt and Bi are coprecipitated; or a case where the aqueous solution containing Bi ions is added or fed to the aqueous dispersion of catalysts carrying Pt on activated carbon. This enables efficient formation of Pt—Bi complexes, thus improving the activity and also preventing metal elution during a liquid-phase oxidation reaction. However, such action is speculated, and it does not limit the scope of the present invention.

Hereinafter, "%" indicates "% by mass" unless stated otherwise.

Step 1 is a step for preparing an aqueous dispersion of a catalyst (hereinafter referred to as Pt/C catalyst) carrying Pt on activated carbon.

The activated carbon is not particularly limited, and as long as it can adsorb and carry Pt, any kind of activated carbon may be used. Examples of activated carbon include vegetable activated carbon such as coconut shell activated carbon, mineral activated carbon such as coal activated carbon, and activated carbon of pulp spent liquor, synthetic resins and organic wastes. In addition, an activation method, a pore distribution and a shape are not particularly limited.

The particle size of Pt carried on activated carbon is not particularly limited; however, from the viewpoint of enhancing the dispersibility and the reaction activity, it is preferably 20 nm or less, more preferably 15 nm or less, and further preferably 10 nm or less; and further, it may be, for example, 1 nm or more.

The amount of carried Pt metal in a catalyst solid content is, from the viewpoint of the reactivity, preferably 0.1% or more, more preferably 1% or more, further preferably 3% or more, and further more preferably 5% or more; and from the viewpoint of enhancing the dispersibility, preferably 20% or less, more preferably 15% or less, and further preferably 10% or less. In addition, the Pt/C catalyst can be prepared by a publicly-known impregnation method or separation-precipitation method, but a commercially available one may also be used.

The aqueous dispersion is prepared by adding and stirring the Pt/C catalyst to and in ion-exchanged water, distilled water, pure water or the like.

The dispersion has a concentration of Pt/C catalyst of, from the viewpoint of the efficiency for subsequent steps, preferably 4% or more, more preferably 5% or more, further preferably 6% or more, and further more preferably 7% or more; and from the viewpoint of the operation, preferably 12% or less, more preferably 9% or less, and further preferably 8% or less.

The temperature for preparation is, from the viewpoint of the economic efficiency, preferably 10° C. or higher, more preferably 15° C. or higher, and further preferably 20° C. or higher; from the viewpoint of preventing modification or cohesion of Pt, preferably 60° C. or lower, more preferably 50° C. or lower, further preferably 40° C. or lower, further more preferably 30° C. or lower, and further more preferably 25° C. or lower.

Step 2 is a step for preparing an aqueous solution containing Bi in an ionic state (hereinafter also referred to as Bi aqueous solution).

An ion source for Bi ion has to be Bi species, which allows Bi salts to be dissolved in water or an acidic aqueous solution; and from this viewpoint, it is at least one selected from bismuth nitrate pentahydrate ($Bi(NO_3)_3 \cdot 5H_2O$), bismuth oxide ($Bi_2O_3$), bismuth carbonate (($BiO)_2CO_3$), and bismuth hydroxide ($Bi(OH)_3$), and more preferably bismuth nitrate pentahydrate.

From the viewpoint of dissolving Bi salts, the Bi aqueous solution preferably contains an acid. The acid to be used may be either of an inorganic acid or an organic acid. The organic acid is, from the viewpoint of preventing metal elution from the prepared catalyst during a liquid-phase oxidation reaction, preferably an acid having a carboxyl group, more preferably one or more selected from acetic acid, formic acid, citric acid and oxalic acid, and further preferably acetic acid. The inorganic acid is, from the viewpoint of preventing metal elution from the prepared catalyst during a liquid-phase oxidation reaction, preferably one or more selected from nitric acid, hydrochloric acid, phosphoric acid and sulfuric acid, and more preferably nitric acid.

The amount of acid to be used in the Bi aqueous solution is, from the viewpoint of dissolving Bi salts, preferably 1% or more, and more preferably 1.5% or more; and from the viewpoint of the economic efficiency, preferably 5% or less, more preferably 4% or less and further preferably 3% or less.

From the viewpoint of preventing metal elution from the prepared catalyst, the blending amount of Bi in the Bi aqueous solution is preferably 0.0001 M or more, more preferably 0.0005 M or more, further preferably 0.001 M or more; and from the same viewpoint, preferably 0.1 M or less, more preferably 0.05 M or less, further preferably 0.03 M or less, further more preferably 0.02 M or less, and further more preferably 0.01 M or less.

From the viewpoint of preventing metal elution from the prepared catalyst, the pH of the Bi aqueous solution is preferably 3.8 or less, more preferably 3.6 or less, further preferably 3.4 or less; and preferably 1.0 or more, more preferably 1.5 or more, further preferably 2.0 or more, and further more preferably 2.5 or more.

The temperature for preparing the Bi aqueous solution is not particularly limited, but it is, from the viewpoint of the economic efficiency, preferably 10° C. or higher, more preferably 15° C. or higher, further preferably 20° C. or higher; and preferably 60° C. or lower, more preferably 50° C. or lower, further preferably 40° C. or lower, further more preferably 30° C. or lower, and further more preferably 25° C. or lower.

Prior to Step 3, either one or both of the aqueous dispersion obtained in Step 1 and the Bi aqueous solution obtained in Step 2; or from the viewpoint of the operation, preferably, a liquid receiving the addition or dropping in Step 3, that is the Bi aqueous solution obtained in Step 2 is, from the viewpoint of preventing metal elution from the prepared catalyst, preferably treated with a reducing agent or reducing gas, which is usable for reducing treatment of Pt in the next Step 3. Treatment with a reducing agent may be carried out by adding formalin or sodium borohydride to the obtained aqueous dispersion or Bi aqueous solution. Further, treatment with reducing gas may be carried out, for example, by producing a reducing atmosphere by circulating reducing gas such as hydrogen or carbon monoxide through the aqueous dispersion or the Bi aqueous solution. Preferably, reducing gas is circulated, and more preferably, hydrogen gas is circulated.

The temperature for treating with a reducing agent or reducing gas is, from the viewpoint of the economic efficiency, preferably 10° C. or higher, more preferably 15° C. or higher, and further preferably 20° C. or higher; and from the viewpoint of preventing modification or cohesion of Pt, preferably 60° C. or lower, more preferably 50° C. or lower, further preferably 40° C. or lower, further more preferably 30° C. or lower, and further preferably 25° C. or lower.

Further, when the treatment is carried out by circulating reducing gas, the feeding amount of reducing gas to be circulated is, from the viewpoint of sufficiently treating with reducing gas, a large excess amount relative to the catalyst, preferably 60 mL/min. or more, and more preferably 80 mL/min. or more; and from the viewpoint of the economic efficiency, preferably 500 mL/min. or less, more preferably 300 mL/min. or less, and further preferably 150 mL/min. or less.

The time period for treating with a reducing agent or reducing gas is, from the viewpoint of sufficiently treating with a reducing agent or reducing gas, preferably 10 minutes or more, more preferably 15 minutes or more, and further preferably 20 minutes or more; and from the viewpoint of the productivity, preferably 2 hours or less, more preferably 1 hour or less, and further preferably 30 minutes or less.

Step 3 is a step, in which the aqueous dispersion obtained in Step 1 is added to the Bi aqueous solution obtained in Step 2.

It is believed that addition of the Pt/C catalyst aqueous dispersion to the Bi aqueous solution enables efficient formation of a complex of Pt—Bi/C catalyst. The addition may be any of continuous addition, divided addition and bulk addition, but continuous addition or divided addition is preferred, and continuous divided addition such as dropping is more preferred.

In the case that continuous addition or continuous divided addition such as dropping is adopted, from the viewpoint of the productivity, the addition rate of the Pt/C catalyst aqueous dispersion is preferably 1 mL/min. or more, and more preferably 3 mL/min. or more; and from the viewpoint of enhancing the activity of the prepared catalyst and the viewpoint of preventing metal elution from the prepared catalyst, the addition rate of the Pt/C catalyst aqueous dispersion is preferably 10 mL/min. or less and more preferably 5 mL/min. or less.

Further, the time period required for the addition is not particularly limited, but it is, from the viewpoint of enhancing the activity of the prepared catalyst and preventing metal elution from the prepared catalyst, preferably 15 minutes or more, more preferably 30 minutes or more, further preferably 1 hour or more, and further more preferably 2 hours or more; and from the viewpoint of the productivity, preferably 10 hours or less, more preferably 7 hours or less, further preferably 5 hours or less, and further more preferably 3 hours or less.

The temperature of the Bi aqueous solution receiving the addition or dropping in Step 3 is, from the viewpoint of enhancing the activity of the prepared catalyst and preventing metal elution from the prepared catalyst, preferably 10° C. or higher, more preferably 15° C. or higher and further preferably 20° C. or higher; and from the viewpoint of preventing modification or cohesion of Pt, preferably 60° C. or lower, more preferably 50° C. or lower, further preferably 40° C. or lower, further more preferably 30° C. or lower, and further more preferably 25° C. or lower.

From the viewpoint of preventing metal elution from the prepared catalyst, reducing treatment is preferably conducted in Step 3. The reducing treatment of Step 3 may be conducted on either one or both of: a liquid to be added or dropped; and a liquid receiving the addition or dropping. However, from the viewpoint of the operation, it is preferably conducted on the liquid receiving the addition or dropping. Regarding the reducing treatment of Step 3, from the viewpoint of preventing metal elution from the prepared catalyst, Step 3 is preferably conducted under a reducing atmosphere. Preferably, the reducing treatment of Step 3 is conducted by circulating reducing gas such as hydrogen or carbon monoxide, more preferably hydrogen gas. Preferable ranges of the reducing treatment temperature and the feed rate of reducing gas when the reducing treatment is conducted by circulating the reducing gas are the same as the respective preferable ranges of the temperature for treating with a reducing agent or reducing gas and the feed rate of the reducing gas, which are applied prior to Step 3. The reducing treatment of Step 3 is conducted preferably until addition of the Pt/C catalyst aqueous dispersion is finished.

The catalyst preparation method of the present invention may have, as Step 4, a step of mixing the catalyst-containing liquid obtained in Step 3 with a reducing adjuvant and obtaining a liquid containing the catalyst carrying Pt and Bi on activated carbon (that is, the above Pt—Bi/C catalyst) and the reducing adjuvant. This step is preferred from the viewpoint of preventing metal elution from the prepared catalyst.

The reducing adjuvant is for maintaining a reduction state of the catalyst carrying Pt and Bi on activated carbon, and organic solvents having a reducing property, such as isopropyl alcohol (IPA) may be used.

From the viewpoint of preventing metal elution from the prepared catalyst, the amount of reducing adjuvant to be used relative to 100 parts by mass of the catalyst-containing liquid obtained in Step 3 is preferably 0.1 parts by mass or more, more preferably 0.5 parts by mass or more, and further preferably 1.0 part by mass or more; and from the viewpoint of the economic efficiency, preferably 10 parts by mass or less, more preferably 5 parts by mass or less, and further preferably 2 parts by mass or less.

The catalyst preparation method of the present invention may have, as Step 5, a step of washing the catalyst carrying Pt and Bi on activated carbon in the liquid obtained in Step 4 with a cleansing liquid. This step is preferred from the viewpoint of the activity of the prepared catalyst and preventing metal elution from the prepared catalyst.

From the viewpoint of enhancing the activity of the prepared catalyst and the viewpoint of preventing metal elution from the prepared catalyst, the cleansing liquid used in Step 5 is preferably a liquid containing one or more selected from water and the above reducing adjuvants, more preferably a liquid containing water and one or more of the above reducing adjuvants, and further preferably an IPA aqueous solution.

From the viewpoint of washing efficiently, the liquid obtained in Step 4 is preferably filtrated before washing so that the catalyst carrying Pt and Bi on activated carbon is separated by filtration. The filtration may be conducted either of under a reduced pressure or under an increased pressure.

The catalyst preparation method of the present invention may have, as Step 6, a step of drying the catalyst carrying Pt and Bi on activated carbon, which has been washed in Step 5. This step is preferred from the viewpoint of the handleability.

The drying is carried out for example under the circulation of an inert gas such as nitrogen gas.

In the catalyst preparation method of the present invention, it is preferred to conduct no neutralization treatment after Step 3 from the viewpoint of enhancing the activity of the prepared catalyst and the viewpoint of preventing metal elution from the prepared catalyst.

The pH of the catalyst-containing liquid obtained in Step 3 is, from the viewpoint of enhancing the activity of the prepared catalyst and the viewpoint of preventing metal elution from the prepared catalyst, preferably 3.8 or less, more preferably 3.6 or less, further preferably 3.4 or less; and preferably 1.0 or more, more preferably 1.5 or more, further preferably 2.0 or more, and further more preferably 2.5 or more.

Further, when Step 4 is conducted, the pH of a filtrate provided by filtration of the liquid obtained in Step 4 is, from the viewpoint of enhancing the activity of the prepared catalyst and the viewpoint of preventing metal elution from the prepared catalyst, preferably 3.8 or less, more preferably 3.6 or less, and further preferably 3.4 or less; and preferably 1.0 or more, more preferably 1.5 or more, further preferably 2.0 or more, and further more preferably 2.5 or more.

Further, when the washing of Step 5 is conducted, the pH of a filtrate after the washing is, from the viewpoint of enhancing the activity of the prepared catalyst and the viewpoint of preventing metal elution from the prepared catalyst, preferably 3.8 or less, more preferably 3.6 or less, and further preferably 3.4 or less; and preferably 1.0 or more, more preferably 1.5 or more, further preferably 2.0 or more, and further preferably 2.5 or more.

The amount of carried Bi in the solid content of Pt—Bi/C catalyst is, from the viewpoint of the productivity improvement of a product of oxidation reaction, preferably 0.01% or more, and more preferably 0.5% or more; and preferably 10% or less, more preferably 5% or less, further preferably 3.5% or less, and further more preferably 1.5% or less.

The mass ratio (atomic ratio) of Bi to Pt, Bi/Pt in the Pt—Bi/C catalyst is, from the viewpoint of the productivity improvement of a product of oxidation reaction, preferably 0.05 or more, and more preferably 0.1 or more; and preferably 1.0 or less, more preferably 0.6 or less, further preferably 0.3 or less, and further more preferably 0.2 or less.

From the viewpoint of enhancing the activity of the prepared catalyst and the viewpoint of preventing metal elution from the prepared catalyst, in the photoelectron spectrum of a Bi4f orbital measured by XPS, the catalyst of the present invention carrying Pt and Bi on activated carbon has a peak top binding energy value in a binding energy range between 162 and 155 eV of, preferably 158.5 eV or less, more preferably 158.2 eV or less, and further preferably 158.0 eV or less; and preferably 157.0 eV or more, more preferably 157.2 eV or more, and further preferably 157.5 eV or more.

The catalyst of the present invention is suitably used for a reaction for producing a carboxyl compound or a ketone compound by oxidizing a hydroxy compound or an aldehyde compound, for example, a reaction for causing liquid-phase oxidation of polyoxyalkylene alkyl ether to produce a corresponding carboxyl compound. That is, the present invention also relates to a method for producing an oxide of alcohol or an oxide of polyoxyalkylene alkyl ether (hereinafter, referred to as the oxide) by feeding, in the presence of the above catalyst, oxygen to a composition containing an alcohol or polyoxyalkylene alkyl ether, and water, and oxidizing by dehydrogenation the alcohol or the polyoxyalkylene alkyl ether. That is, the present invention relates to a method for producing the oxide, which has a step for obtaining the above catalyst; and a step for feeding, in the presence of the catalyst, oxygen to a composition containing an alcohol or polyoxyalkylene alkyl ether, and water, and oxidizing by dehydrogenation the alcohol or the polyoxyalkylene alkyl ether.

The alcohol or the polyoxyalkylene alkyl ether is preferably one kind, or two or more kinds represented by the following general formula (1) or general formula (2).

$$R^1O-H \quad (1)$$

In the general formula (1), $R^1$ is an aliphatic hydrocarbon group having a carbon number of 2 or more and 40 or less.

$$R^2O-(AO)_n-H \quad (2)$$

In the general formula (2), $R^2$ is a hydrocarbon group having a carbon number of 2 or more and 40 or less; AO denotes an alkyleneoxy group having a carbon number of 2 or more and 4 or less; and n denotes a number of moles added of alkyleneoxy group and is an integer of 1 or more and 30 or less.

From the view point of the reactivity, $R^1$ is preferably a liner or branched, primary or secondary aliphatic hydrocarbon group, more preferably a linear or branched, primary or secondary alkyl group or alkenyl group, and further preferably a linear, primary or secondary alkyl group.

The carbon number of $R^1$ is not particularly limited, but it may be 6 or more, 8 or more, 10 or more, or 12 or more; and from the viewpoint of the reactivity, it is preferably 36 or less, more preferably 22 or less, further preferably 18 or less, and further more preferably 14 or less.

From the viewpoint of the reactivity, $R^2$ is preferably an aliphatic hydrocarbon group, more preferably a liner or branched, primary or secondary aliphatic hydrocarbon group, further preferably a liner or branched, primary or secondary alkyl group or alkenyl group, and further more preferably a linear, primary or secondary alkyl group.

The carbon number of $R^2$ is not particularly limited, but it may be 6 or more, 8 or more, 10 or more, or 12 or more; and from the viewpoint of the reactivity, it is preferably 36 or less, more preferably 22 or less, further preferably 18 or less, and further more preferably 14 or less.

The mass ratio of the alcohol or the polyoxyalkylene alkyl ether used as a raw material relative to water used for reaction (alcohol or polyoxyalkylene alkyl ether used as a raw material/water) is, from the viewpoint of the productivity improvement of an oxide of alcohol or an oxide of polyoxyalkylene alkyl ether; and the prevention of viscosity increase of a liquid phase, preferably 60/40 or more, more preferably 70/30 or more, and further preferably 75/25 or more; and preferably 95/5 or less, more preferably 90/10 or less, and further preferably 85/15 or less.

Oxygen may be fed to the composition or a liquid phase as a reaction solution thereof by circulating an oxygen-containing gas in the liquid phase. Examples of the oxygen-containing gas include oxygen gas and oxygen-containing mixed gases such as air.

When an oxygen-containing mixed gas is used, a gas to be used in combination with oxygen is, from the viewpoint of providing no influence on the activity, preferably an inert gas such as helium, argon and nitrogen.

The oxygen concentration in the oxygen-containing gas is, from the viewpoint of the productivity of the oxide, preferably 10% by volume or more, more preferably 50% by volume or more, further preferably 70% by volume or more, further more preferably 90% by volume or more, further more preferably substantially 100% by volume, and further more preferably 100% by volume.

Such production may be conducted by a continuous system, a batch system or a semi-batch system.

The reaction temperature is, from the viewpoint of the reactivity, preferably 50° C. or higher, and more preferably 60° C. or higher; and from the viewpoint of the facility load, preferably 100° C. or lower, more preferably 90° C. or lower, and further preferably 80° C. or lower.

The reaction may be conducted under a normal pressure or under an increased pressure. The reaction pressure is, from the viewpoint of the reactivity, as expressed in absolute pressure, preferably 0.09 MPa or more, and more preferably 0.10 MPa or more; and from the viewpoint of the facility load, preferably 0.5 MPa or less, more preferably 0.2 MPa or less, and further preferably 0.11 MPa or less.

The amount of catalyst to be used is dependent on the reaction temperature or the reaction pressure, and it can be determined arbitrarily within such range that a practical reaction rate is achieved. However, when the reaction is caused by a batch system, the amount is, from the viewpoint of the reactivity, as a mass of Pt metal relative to 100 parts by mass of polyoxyalkylene alkyl ether, preferably 0.1 parts by mass or more, more preferably 1 part by mass or more, further preferably 3 parts by mass or more, and further more preferably 6 parts by mass or more; and from the viewpoint of the economic efficiency, preferably 20 parts by mass or less, more preferably 15 parts by mass or less, and further preferably 10 parts by mass or less.

Hereinafter, preferable embodiments of the present invention are described.

<1> A method for preparing a catalyst, having the following Steps 1, 2 and 3.

Step 1: preparing an aqueous dispersion of a catalyst (Pt/C catalyst) carrying Pt on activated carbon;

Step 2: preparing an aqueous solution (Bi aqueous solution) containing Bi in an ionic state; and Step 3: adding the aqueous dispersion obtained in Step 1 to the aqueous solution obtained in Step 2.

<2> The preparation method described in <1>, wherein Pt may have a particle diameter of preferably 20 nm or less, more preferably 15 nm or less, and further preferably 10 nm or less; and 1 nm or more.

<3> The preparation method described in <1> or <2>, wherein the amount of carried Pt metal in a catalyst solid content is preferably 0.1% or more, more preferably 1% or more, further preferably 3% or more, and further more preferably 5% or more; and preferably 20% or less, more preferably 15% or less, and further preferably 10% or less.

<4> The preparation method described in any one of <1> to <3>, wherein the concentration of Pt/C catalyst in the aqueous dispersion is preferably 4% or more, more preferably 5% or more, further preferably 6% or more, and further more preferably 7% or more; and preferably 12% or less, more preferably 9% or less, and further preferably 8% or less.

<5> The preparation method described in any one of <1> to <4>, wherein the preparation temperature of Step 1 is preferably 10° C. or more, more preferably 15° C. or higher, and further preferably 20° C. or higher; and preferably 60° C. or lower, more preferably 50° C. or lower, further preferably 40° C. or lower, further more preferably 30° C. or lower and further more preferably 25° C. or lower.

<6> The preparation method described in any one of <1> to <5>, wherein an ion source for the Bi ion is preferably at least one selected from bismuth nitrate pentahydrate (Bi(NO$_3$)$_3$.5H$_2$O), bismuth oxide (Bi$_2$O$_3$), bismuth carbonate ((BiO)$_2$CO$_3$), and bismuth hydroxide (Bi(OH)$_3$), and more preferably bismuth nitrate pentahydrate.

<7> The preparation method described in any one of <1> to <6>, wherein the aqueous solution obtained in Step 2 contains an acid.

<8> The preparation method described in <7>, wherein the acid is an inorganic acid or an organic acid, preferably an organic acid, more preferably an acid having a carboxyl group, further preferably one or more selected from acetic acid, formic acid, citric acid and oxalic acid, and further more preferably acetic acid.

<9> The preparation method described in <7>, wherein the acid is an inorganic acid, preferably one or more selected from nitric acid, hydrochloric acid, phosphoric acid and sulfuric acid, and more preferably nitric acid.

<10> The catalyst preparation method described in <7>, wherein the acid is one selected from acetic acid and nitric acid.

<11> The preparation method described in any one of <7> to <10>, wherein the amount of acid to be used in the Bi aqueous solution is preferably 1% or more, and more preferably 1.5% or more; and preferably 5% or less, more preferably 4% or less and further preferably 3% or less.

<12> The preparation method described in any one of <1> to <11>, wherein the amount of Bi to be blended in the Bi aqueous solution is preferably 0.0001 M or more, more preferably 0.0005 M or more, and further preferably 0.001 M or more; and preferably 0.1 M or less, more preferably 0.05 M or less, further preferably 0.03 M or less, further more preferably 0.02 M or less, and further more preferably 0.01 M or less.

<13> The preparation method described in any one of <1> to <12>, wherein the Bi aqueous solution has a pH of preferably 3.8 or less, more preferably 3.6 or less, and further preferably 3.4 or less; and preferably 1.0 or more, more preferably 1.5 or more, further preferably 2.0 or more, and further more preferably 2.5 or more.

<14> The preparation method described in any one of <1> to <13>, wherein the Bi aqueous solution is prepared at a temperature of preferably 10° C. or higher, more preferably 15° C. or higher, and further preferably 20° C. or higher; and preferably 60° C. or lower, more preferably 50° C. or lower, further preferably 40° C. or lower, further more preferably 30° C. or lower, and further more preferably 25° C. or lower.

<15> The preparation method described in any one of <1> to <14>, wherein either one or both of the aqueous dispersion obtained in Step 1 and the Bi aqueous solution obtained in Step 2, preferably a liquid receiving the addition or dropping in Step 3, that is the Bi aqueous solution obtained in Step 2, is treated with a reducing agent or reducing gas prior to Step 3.

<16> The preparation method described in <15>, wherein the treatment with a reducing agent or reducing gas is conducted at a temperature of preferably 10° C. or higher, more preferably 15° C. or higher, and further preferably 20° C. or higher; and preferably 60° C. or lower, more preferably 50° C. or lower, further preferably 40° C. or lower, further more preferably 30° C. or lower, and further more preferably 25° C. or lower.

<17> The preparation method described in <15> or <16>, wherein the treatment with a reducing agent or reducing gas is conducted for preferably 10 minutes or more, more preferably 15 minutes or more, and further preferably 20 minutes or more; and preferably 2 hours or less, more preferably 1 hour or less, and further preferably 30 minutes or less.

<18> The preparation method described in any one of <15> to <17>, wherein the treatment with a reducing agent or reducing gas is conducted by circulating reducing gas, preferably hydrogen gas.

<19> The preparation method described in <18>, wherein the reducing gas is fed at a rate of preferably 60 mL/min. or more, more preferably 80 mL/min. or more, and further preferably 120 mL/min. or more; and preferably 500 mL/min. or less, more preferably 300 mL/min. or less, and further preferably 150 mL/min. or less.

<20> The preparation method described in any one of <1> to <19>, wherein the addition in Step 3 is conducted by continuous addition, divided addition, bulk addition or continuous divided addition, preferably continuous addition, divided addition or continuous divided addition, and more preferably dropping.

<21> The preparation method described in any one of <1> to <20>, wherein the Pt/C catalyst aqueous dispersion is added at a rate of preferably 1 mL/min. or more, and more preferably 3 mL/min. or more; and preferably 10 mL/min. or less, and more preferably 5 mL/min. or less.

<22> The preparation method described in any one of <1> to <21>, wherein the time period required for addition is preferably 15 minutes or more, more preferably 30 minutes or more, further preferably 1 hour or more, and further more preferably 2 hours or more; and preferably 10 hours or less, more preferably 7 hours or less, further preferably 5 hours or less, and further more preferably 3 hours or less.

<23> The preparation method described in any one of <1> to <22>, wherein the Bi aqueous solution receiving the addition in Step 3 has a temperature of preferably 10° C. or higher, more preferably 15° C. or higher, and further preferably 20° C. or higher; and preferably 60° C. or lower, more preferably 50° C. or lower, further preferably 40° C. or lower, further more preferably 30° C. or lower, and further more preferably 25° C. or lower.

<24> The preparation method described in any one of <1> to <23>, wherein reducing treatment is preferably conducted in Step 3, the reducing treatment of Step 3 is conducted on either one or both of the liquid to be added or dropped and the liquid receiving the addition or dropping, preferably on the liquid receiving the addition or dropping, and the reducing treatment of Step 3 is preferably to conduct Step 3 under a reducing atmosphere.

<25> The preparation method described in <24>, wherein the reducing treatment of Step 3 is conducted preferably until the end of addition of the Pt/C catalyst aqueous dispersion.

<26> The preparation method described in <24> or <25>, wherein the reducing treatment of Step 3 is conducted at a temperature of preferably 10° C. or higher, more preferably 15° C. or higher, and further preferably 20° C. or higher; and preferably 60° C. or lower, more preferably 50° C. or lower, further preferably 40° C. or lower, further more preferably 30° C. or lower, and further more preferably 25° C. or lower.

<27> The preparation method described in any one of <24> to <26>, wherein the reducing treatment of Step 3 is conducted by circulating a reducing gas, preferably hydrogen gas.

<28> The preparation method described in <27>, wherein the reducing gas in Step 3 is fed at a rate of preferably 60 mL/min. or more, more preferably 80 mL/min. or more, and further preferably 120 mL/min. or more; and preferably 500 mL/min. or less, more preferably 300 mL/min. or less, and further preferably 150 mL/min. or less.

<29> The preparation method described in any one of <1> to <28>, wherein no neutralization treatment is conducted after Step 3.

<30> The preparation method described in any one of <1> to <29>, wherein the catalyst-containing liquid obtained in Step 3 has a pH of preferably 3.8 or less, more preferably 3.6 or less, and further preferably 3.4 or less; and preferably 1.0 or more, more preferably 1.5 or more, and further preferably 2.0 or more, and further more preferably 2.5 or more.

<31> The preparation method described in any one of <1> to <30>, wherein the method has Step 4 for mixing the catalyst-containing liquid obtained in Step 3 and a reducing adjuvant with each other to obtain a liquid containing a catalyst (Pt—Bi/C catalyst) carrying Pt and Bi on activated carbon and the reducing adjuvant.

<32> The preparation method described in <31>, wherein the reducing adjuvant is preferably an organic solvent having a reducing property, more preferably isopropyl alcohol (IPA).

<33> The preparation method described in <31> or <32>, wherein the reducing adjuvant is used in an amount, relative to 100 parts by mass of the catalyst-containing liquid obtained in Step 3, of preferably 0.1 parts by mass or more, more preferably 0.5 parts by mass or more, and further preferably 1.0 part by mass or more; and preferably 10 parts by mass or less, more preferably 5 parts by mass or less, and further preferably 2 parts by mass or less.

<34> The preparation method described in any one of <31> to <33>, wherein a filtrate obtained by filtering the liquid obtained in Step 4 has a pH of preferably 3.8 or less, more preferably 3.6 or less, and further preferably 3.4 or less; and preferably 1.0 or more, more preferably 1.5 or more, further preferably 2.0 or more, and further more preferably 2.5 or more.

<35> The preparation method described in any one of <31> to <34>, wherein the method has Step 5 for washing, with a cleansing liquid, the catalyst carrying Pt and Bi on activated carbon in the liquid obtained in Step 4.

<36> The preparation method described in <35>, wherein the cleansing liquid is preferably a liquid containing one or more selected from water and reducing adjuvants, more preferably a liquid containing water and one or more kinds of reducing adjuvant, and further preferably an IPA aqueous solution.

<37> The preparation method described in <35> or <36>, wherein, before the washing, the liquid obtained in Step 4 is filtered to separate the catalyst carrying Pt and Bi on activated carbon.

<38> The preparation method described in any one of <35> to <37>, wherein the filtrate after the washing of Step 5 has a pH of preferably 3.8 or less, more preferably 3.6 or less, and further preferably 3.4 or less; and preferably 1.0 or more, more preferably 1.5 or more, further preferably 2.0 or more, and further more preferably 2.5 or more.

<39> The preparation method described in any one of <35> to <38>, wherein the method has Step 6 for drying the catalyst carrying Pt and Bi on activated carbon, which is washed in Step 5.

<40> The preparation method described in <39>, wherein the drying is conducted under the circulation of preferably an inert gas, more preferably nitrogen gas.

<41> A Pt—Bi/C catalyst obtained by the method described in any one of <1> to <40>.

<42> The catalyst described in <41>, wherein the amount of carried Bi in a solid content of the Pt—Bi/C catalyst is preferably 0.01% or more, and more preferably 0.5% or more; and preferably 10% or less, more preferably 5% or less, further preferably 3.5% or less, and further more preferably 1.5% or less.

<43> The catalyst described in <41> or <42>, wherein the Pt—Bi/C catalyst has a mass ratio (atomic ratio) of Bi to Pt, Bi/Pt, of preferably 0.05 or more, and more preferably 0.1 or more; and preferably 1.0 or less, more preferably 0.6 or less, further preferably 0.3 or less, and further more preferably 0.2 or less.

<44> A catalyst carrying Pt and Bi on activated carbon, wherein, in the photoelectron spectrum of a Bi4f orbital measured by XPS, a peak top binding energy value in a binding energy range between 162 and 155 eV is preferably 158.5 eV or less, more preferably 158.2 eV or less, and further preferably 158.0 eV or less; and preferably 157.0 eV or more, more preferably 157.2 eV or more, and further preferably 157.5 eV or more.

<45> A method for producing an oxide of alcohol or an oxide of polyoxyalkylene alkyl ether, including: feeding, in the presence of the catalyst described in any one of <41> to <44>, oxygen to a composition containing an alcohol or polyoxyalkylene alkyl ether, and water; and oxidizing by dehydrogenation the alcohol or the polyoxyalkylene alkyl ether.

<46> The method for producing an oxide of alcohol or an oxide of polyoxyalkylene alkyl ether described in <45>, wherein the alcohol or the polyoxyalkylene alkyl ether is one kind or two or more kinds represented by the following general formula (1) or general formula (2),

$$R^1O\text{—}H \quad (1)$$

in the general formula (1), $R^1$ is an aliphatic hydrocarbon group having a carbon number of 2 or more and 40 or less,

$$R^2O\text{-}(AO)_n\text{—}H \quad (2)$$

in the general formula (2), $R^2$ is a hydrocarbon group having a carbon number of 2 or more and 40 or less; AO denotes an alkyleneoxy group having a carbon number of 2 or more and 4 or less; and n denotes a number of moles added of alkyleneoxy group and is an integer of 1 or more and 30 or less.

<47> The method for producing an oxide described in <46>, wherein $R^1$ is preferably a liner or branched, primary or secondary aliphatic hydrocarbon group, more preferably a linear or branched, primary or secondary alkyl group or alkenyl group, and further preferably a linear, primary or secondary alkyl group.

<48> The method for producing an oxide described in <46> or <47>, wherein $R^1$ has a carbon number of 6 or more, 8 or more, 10 or more, or 12 or more; and preferably 36 or less, more preferably 22 or less, further preferably 18 or less, and further more preferably 14 or less.

<49> The method for producing an oxide described in any one of <46> to <48>, wherein $R^2$ is preferably an aliphatic hydrocarbon group, more preferably a liner or branched, primary or secondary aliphatic hydrocarbon group, further preferably a liner or branched, primary or secondary alkyl group or alkenyl group, and further more preferably a linear, primary or secondary alkyl group.

<50> The method for producing an oxide described in any one of <46> to <49>, wherein $R^2$ has a carbon number of 6 or more, 8 or more, 10 or more, or 12 or more; and preferably 36 or less, more preferably 22 or less, further preferably 18 or less, and further more preferably 14 or less.

<51> The method for producing an oxide described in any one of <45> to <50>, wherein the mass ratio of the alcohol or the polyoxyalkylene alkyl ether relative to water used for reaction is preferably 60/40 or more, more preferably 70/30 or more, and further preferably 75/25 or more; and preferably 95/5 or less, more preferably 90/10 or less, and further preferably 85/15 or less.

<52> The method for producing an oxide described in any one of <45> to <51>, wherein oxygen is fed to the composition or a liquid phase as a reaction solution thereof by circulating an oxygen-containing gas in the liquid phase, and the oxygen-containing gas is preferably oxygen gas or a mixed gas such as air.

<53> The method for producing an oxide described in <52>, wherein the oxygen-containing gas has an oxygen concentration of preferably 10% by volume or more, more preferably 50% by volume or more, further preferably 70% by volume or more, further more preferably 90% by volume, further more preferably substantially 100% by volume, and further more preferably 100% by volume.

<54> The method for producing an oxide described in any one of <45> to <53>, wherein the reaction temperature is preferably 50° C. or higher, and more preferably 60° C. or higher; and preferably 100° C. or lower, more preferably 90° C. or lower, and further preferably 80° C. or lower.

<55> The method for producing an oxide described in any one of <45> to <54>, wherein the reaction pressure is preferably 0.09 MPa or more, and more preferably 0.10 MPa or more; and preferably 0.5 MPa or less, more preferably 0.2 MPa or less, and further preferably 0.11 MPa or less.

<56> The method for producing an oxide described in any one of <45> to <55>, wherein the amount of catalyst to be used is, in terms of the mass of Pt metal relative to 100 parts by mass of polyoxyalkylene alkyl ether, preferably 0.1 parts by mass or more, more preferably 1 part by mass or more, further preferably 3 parts by mass or more, and further more preferably 6 parts by mass or more; and preferably 20 parts by mass or less, more preferably 15 parts by mass or less, and further preferably 10 parts by mass or less.

<57> Use of the catalyst described in any one of <41> to <44> as a dehydrogenation-oxidation catalyst for an alcohol or a polyoxyalkylene alkyl ether.

EXAMPLES

In the following Examples and Comparative Examples, the temperature condition is 20° C., the stirring condition is 200 rpm, and the pressure condition is a normal pressure, unless otherwise stated. Further, for pH measurement, pH test paper "Roll type UNIV" manufactured by ADVANTEC was used.

Example 1

<Preparation of 10% Pt-1% Bi/C Catalyst>
Step 1: Preparation of Pt/C Slurry (Hereinafter Referred to as Liquid A):

40 g of 10% Pt/C (manufactured by Evonik Japan, Pt particle size: 14 nm, water content: 59.2%) and 500 g of ion-exchanged water were fed into a 1 L beaker, and were stirred under a condition of about 100 rpm by use of "Fine Stirrer F-202" (manufactured by Tokyo Garasu Kikai Kabushiki Kaisha) so that solids do not precipitate on a bottom of the beaker.

Step 2: Preparation of an Acidic Aqueous Solution Containing Bismuth (Hereinafter Referred to as Liquid B)

0.38 g of bismuth nitrate pentahydrate (manufactured by Wako Pure Chemical Industries, Ltd.) and 808 mL of 2% acetic acid aqueous solution were fed into a 2 L separable flask provided with a mechanical stirrer "Teflon (registered trademark) stirring blades with a crescent shape" (manufactured by AS ONE Corporation, stirring blade with 75 mm width×20 mm height×4 mm thickness). The 2% acetic acid aqueous solution had a Bi concentration of 0.001 M. In order to dissolve bismuth salts completely, ultrasonic waves were applied for 5 minutes under the condition of a frequency of 38 kHz by an ultrasonic cleaner "Fine Ultrasonic Cleaner FU-9H" (manufactured by Tokyo Garasu Kikai Kabushiki Kaisha).

Prior to Step 3, Liquid B in the separable flask, which would receive a dropwise addition in Step 3, was subjected to hydrogen substitution by circulating hydrogen at a rate of 86 to 129 mL/min. for 20 minutes while stirring by a mechanical stirrer under the condition of 200 rpm.

Thereafter, 2 mL of acetic acid was added while stirring under hydrogen circulation. After the addition of acetic acid, the solution had a pH of 3.

Step 3:

While hydrogen circulation and stirring were continuing for Liquid B in the separable flask, Liquid A in the beaker was dropped to Liquid B in the separable flask by use of a peristaltic pump. The dropping was conducted while hydrogen was circulated in Liquid B at a rate of 86 to 129 mL/min. and Liquid B was stirred. The dropping rate and dropping time period of Liquid A to be dropped and the temperature of Liquid B receiving the dropping, are as described in Table 1. Further, the solution after the dropping had a pH of 3.

After the dropping was finished, ageing was conducted for 5 minutes and 18 mL of isopropyl alcohol (hereinafter referred to as IPA) was added to maintain a reduction state of a metal. Ageing and addition of IPA were conducted while hydrogen circulation and stirring were continuing for Liquid B. After the addition of IPA, hydrogen circulation was stopped and vacuum filtration was conducted while nitrogen was circulated. This filtration was conducted under suction with a membrane filter "PTFE Membrane Filter T020A142C" (manufactured by ADVANTEC, pore size: 0.2 µm) placed on a filter holder for vacuum filtration "Glass Type KGS-90" (manufactured by ADVANTEC) while the solution after the addition of IPA was allowed to flow, and solids were separated. The resultant filtrate had a pH of 3.

The solids after the filtration were returned to the separable flask, 1% IPA aqueous solution (300 mL) was added, and washing was conducted for 30 minutes while stirring. Thereafter, the filtration was conducted in the same manner as above, solids obtained by the filtration were dried for about one hour, and 10% Pt-1% Bi/C catalyst was obtained. The operations for stirring and washing, filtration, and drying were conducted under nitrogen circulation. Further, the filtrate obtained by filtration conducted after the washing and before the drying had a pH of 3 to 4.

Comparative Example 1

<Preparation 2 of 10% Pt-1% Bi/C Catalyst>
Step 1: Preparation of Pt/C Slurry (Hereinafter Referred to as Liquid A):

40 g of 10% Pt/C (manufactured by Evonik Japan, water content: 59.2%) and 500 g of ion-exchanged water were fed into a 2 L separable flask provided with a mechanical stirrer "Teflon (registered trademark) stirring blades with a crescent shape" (manufactured by AS ONE Corporation, stirring blade with 75 mm width×20 mm height×4 mm thickness).
Step 2: Preparation of an Acidic Aqueous Solution Containing Bismuth (Hereinafter Referred to as Liquid B)

0.38 g of bismuth nitrate pentahydrate (manufactured by Wako Pure Chemical Industries, Ltd.) and 808 mL of 2% acetic acid aqueous solution were fed into a 1 L beaker. The 2% acetic acid aqueous solution had a Bi concentration of 0.001 M. In order to dissolve bismuth salts completely, ultrasonic waves were applied for 5 minutes under the condition of a frequency of 38 kHz by an ultrasonic cleaner "Fine Ultrasonic Cleaner FU-9H" (manufactured by Tokyo Garasu Kikai Kabushiki Kaisha).

Prior to Step 3, Liquid A in the separable flask, which would receive a dropwise addition in Step 3, was subjected to hydrogen substitution by circulating hydrogen at a rate of 86 to 129 mL/min. for 20 minutes while stirring by a mechanical stirrer under the condition of 200 rpm. Thereafter, 2 mL of acetic acid was added while stirring under hydrogen circulation. After the addition of acetic acid, the solution had a pH of 3.

Step 3:

While hydrogen circulation and stirring were continuing for Liquid A in the separable flask, Liquid B in the beaker was dropped to Liquid A in the separable flask by use of a peristaltic pump. The dropping rate and dropping time period of Liquid B to be dropped, and the temperature of Liquid A receiving the dropwise addition are as described in Table 1. Further, the solution after the dropping had a pH of 4.

After the dropping was finished, ageing was conducted for 5 minutes while hydrogen circulation and stirring were continuing; and 18 mL of isopropyl alcohol (hereinafter referred to as IPA) was added to maintain a reduction state of a metal. After the addition of IPA, hydrogen circulation was stopped and vacuum filtration was conducted while nitrogen was circulated. This filtration was conducted under suction with a membrane filter "PTFE Membrane Filter T020A142C" (manufactured by ADVANTEC, pore size: 0.2 µm) placed on a filter holder for vacuum filtration "Glass Type KGS-90" (manufactured by ADVANTEC) while the solution after the addition of IPA was allowed to flow, and solids were separated. The resultant filtrate had a pH of 3 to 4.

The solids after the filtration were returned to the separable flask, 1% IPA aqueous solution (300 mL) was further added, and washing was conducted for 30 minutes while stirring. Thereafter, the filtration was conducted in the same manner as above, solids obtained by the filtration were dried for about one hour, and 10% Pt-1% Bi/C catalyst was obtained. The operations for stirring and washing, filtration, and drying were conducted under nitrogen circulation. Further, the filtrate obtained by filtration conducted after washing and before drying had a pH of 3 to 4.

Example 2

A catalyst was obtained by conducting the same steps as in Example 1 except that a Pt/C catalyst with an amount of carried Pt of 5% was used and neutralization, washing and filtration were conducted after IPA addition and filtration. The filtration was conducted by the method described in Example 1. Further, neutralization and washing were conducted as follows.

After IPA addition and filtration, filtrated solids were returned to the separable flask, 300 mL of 0.05 M $NaHCO_3$ aqueous solution was added, and the resultant was stirred for 30 minutes and neutralized. Thereafter, filtration was conducted, solids were returned to the separable flask, 300 mL of ion-exchanged water was further added, and the resultant was stirred for 30 minutes and washed. Operations for neutralization and washing were conducted under nitrogen circulation. Further, the filtrate immediately after neutralization and the filtrate after washing had a pH of 7.

Comparative Example 2

A catalyst was obtained by conducting the same steps as in Comparative Example 1 except that a Pt/C catalyst with an amount of carried Pt of 5% was used and neutralization, washing and filtration were conducted after IPA addition and filtration. The filtration was conducted by the method described in Comparative Example 1. Further, neutralization and washing were conducted by the same steps as in Example 2.

In conducting a performance assessment of a catalyst, an amount of ion-exchanged water to be fed is determined. For that purpose, it is necessary to measure a water content in a catalyst. Water contents in catalysts obtained in Example 1, Comparative Example 1, Example 2 and Comparative Example 2 were measured by the following method. Obtained results are shown in Tables 1 and 2.

<Method for Measuring a Water Content in a Catalyst>

The water content in a catalyst is determined by drying the catalyst and measuring weights of the catalyst before and after drying as described below.

About 3 g of catalyst was placed on a petri dish "Flat Shale FS-90B" (manufactured by VIDREX), and the weight thereof was measured. Thereafter, "VACUUM DRYING OVEN DRR420DA" (manufactured by ADVANTEC) was used to reduce a pressure to −80 kPa to −100 kPa; vacuum drying was conducted at 70° C. for 4 hours; and the weight thereof was measured again. Assuming that a decrease of the weight was equivalent to water contained in the catalyst, the water content was determined by the following equation.

(Water content (%) in catalyst)=100×(Weight decrease (g))/(Weight (g) of catalyst before drying)

Catalysts obtained in Example 1, Comparative Example 1, Example 2 and Comparative Example 2 were used to produce ether carboxylate by the following method, and amounts of metal elution from the catalysts and yields of ether carboxylate were measured. Measured results are shown in Tables 1 and 2.

<Production of Ether Carboxylate>

265 g of polyoxyethylene alkyl ether (obtained by adding 3.6 mols of ethylene oxide on average to lauryl alcohol) as a raw material; such an amount of catalyst that the total metal amount of Pt and Bi in the catalyst is 6.4 parts by mass for Example 1 and Comparative Example 1 and 3.2 parts by mass for Example 2 and Comparative Example 2 relative to 100 parts by mass of the raw material; and an amount (g) of ion-exchanged water to be fed determined by the following calculation method were fed into a 500 mL seven-necked flask provided with a reflux tube, a pH meter "Digital pH controller FD-02" (manufactured by Tokyo Garasu Kikai Kabushiki Kaisha), a dissolved oxygen meter "InPro 6850i/12/220" (manufactured by METTLER TOLEDO) and a mechanical stirrer "Teflon (registered trademark) stirring blades with a crescent shape" (manufactured by AS ONE Corporation, stirring blade with 75 mm width×20 mm height×4 mm thickness).

<Method for Calculating an Amount of Water to be Fed>

Calculation is made as follows so that the amount of water relative to a raw material is 80.9:19.1.

(Amount (g) of water to be fed)=191×(Amount (g) of raw material to be fed)/809−(Water content (%) in catalyst)×(Amount (g) of catalyst to be fed)

While the raw material, catalyst and water fed into the seven-necked flask were stirred under the condition of 450 rpm by the mechanical stirrer, they were heated to 70° C. under nitrogen circulation; and nitrogen was continuously circulated for 15 minutes after they reached 70° C. Thereafter, nitrogen was switched to oxygen, and then the oxygen was circulated for 8 hours at a rate of 90 mL/min. to bring about a reaction. Then, a corresponding ether carboxylate was obtained.

After the end of the reaction, the resultant solution was promptly filtrated under an increased pressure at 70° C., so that the catalyst was separated. For filtration under an increased pressure, a filter was heated in advance to 70° C., and the solution (70° C.) after the end of the reaction was poured into the filter while nitrogen was injected with a pressure of 4 kgf/cm$^2$.

The obtained filtrate was used to determine an amount of metal elution from a catalyst and a yield of ether carboxylate by the following methods.

<Amount of Metal Elution>

ICP analysis was conducted under the following measurement conditions, and amounts of eluted Pt and Bi from a catalyst were measured.

Reagents

Hydrochloric acid: for atomic absorption analysis, manufactured by Kanto Chemical Co., Inc.

Nitric acid: for atomic absorption analysis, manufactured by Kanto Chemical Co., Inc.

Sulfuric acid: for precision analysis, manufactured by Wako Pure Chemical Industries, Ltd.

Pt standard solution: 1000 mg/L standard solution for atomic absorption analysis, manufactured by Kanto Chemical Co., Inc.

Bi standard solution: 1000 mg/L standard solution for atomic absorption analysis, manufactured by Kanto Chemical Co., Inc.

Ultrapure water: Milli-Q water, manufactured by Millipore

Preparation of Sample Solution:

(1) 0.1 g of sample was taken in a ceramic crucible and calcined by a heater, and then 8 mL of aqua regia (hydrochloric acid:nitric acid=3:1) was added and the sample was heated and dissolved. After being cooled, the sample was filtrated and diluted with ultrapure water to 100 mL in total.

(2) A filtration residue was ashed together with filter paper (completely ashed at 550° C. by suitably adding sulfuric acid in the middle) and dissolved with aqua regia in the same manner as in (1); and after being cooled, it was filtrated and diluted to a certain amount in total.

(3) Bi amount and Pt amount were measured for each of the liquids prepared in (1) and (2) and totals of the respective elements were calculated.

(4) The filtration residue of (2) was quantitatively analyzed by fluorescent X-rays, and it was confirmed that no Pt and Bi remained.

Preparation of Solutions for Calibration Curve:

Standard solutions for atomic absorption analysis (Pt and Bi: 1000 mg/L) were used to prepare calibration curve solutions for 0.1 to 2.0 mg/L. Aqua regia was added to each solution so that the solution contains a similar amount of aqua regia (about 8%) as the sample.

Conditions for ICP Measurement

Analytical apparatus: iCAP 6500 Duo manufactured by ThermoFisher Scientific Inc.

Wavelength: 214.423 nm for Pt, 223.061 nm for Bi

RF power: 1150 W

Flow rate of coolant gas: 12 L/min.

Flow rate of nebulizer: 0.70 L/min.

Auxiliary gas: 0.5 L/min.

Pumping rate: 50 rpm

<Yield of Ether Carboxylate>

Under the following measurement conditions, peak areas of the raw material and aldehyde and ether carboxylate as intermediates were obtained by gas chromatography (GC) analysis. A ratio of the peak area of ether carboxylate to total of peak areas of three components was calculated as a yield of ether carboxylate, and expressed in terms of percentage.

Preparation of Solutions Used for GC Analysis
(1) 0.22 g of filtrate was measured and taken in a screw tube; ion-exchanged water and saturated saline solution were added respectively in an amount of 3 mL; 10 mL of diethyl ether was added; and the resultant mixture was separated by layer.
(2) 2.5 mL of ether layer therefrom was measured and taken in a screw tube and methyl-esterified with diazomethane.
(3) Nitrogen was circulated to distill diazomethane.
(4) The solution was concentrated to 1.5 mL to provide a solution to be used for GC analysis.

Conditions for GC Measurement
Apparatus: Agilent Technologies 19091A-102E (manufactured by Agilent Technologies)
Column: Ultra1 Methyl Siloxane (25.0 m×200 μm×0.33 μm)
Injection temp.: 325° C.
Detector temp.: 300° C.
Temperature Program
Initial temp.: 100° C.
Initial time.: 5 min.
Increasing rate: 5° C./min.
Final temp.: 300° C.
Final time: 45 min.
Injection volume: 1.0 μL
Split ratio: 25:1
Total flow rate: 28.1 mL/min. (He)

Results for the above measurements are shown in Tables 1 and 2.

TABLE 1

| | | | Example 1 | Comparative Example 1 |
|---|---|---|---|---|
| Step 1 | Liquid A: Pt/C catalyst aqueous dispersion | Pt amount in Pt/C catalyst [%] | 10 | 10 |
| | | Amount of fed catalyst [g] | 40 | 40 |
| | | Amount of fed water [mL] | 500 | 500 |
| Step 2 | Liquid B: Bi acidic solution | Bi in 2% AcOH aqueous solution [M] | 0.001 | 0.001 |
| | | Amount of fed 2% AcOH aqueous solution [mL] | 808 | 808 |
| | | pH at 20° C. | 3 | 3 |
| Step 3 | | Liquid to be dropped | Liquid A | Liquid B |
| Step 3' | | Dropping rate of liquid to be dropped [mL/min.] | 3.4 | 3.4 |
| | | Period for dropping [h] | 2.5 | 4 |
| | | Liquid receiving the dropping | Liquid B | Liquid A |
| | | Amount of AcOH to be added to liquid receiving the dropping [mL] | 2 | 2 |
| | | Temperature of liquid receiving the dropping [° C.] | 20 | 20 |
| | | Water content in catalyst [%] | 22.9 | 54.7 |
| Effects | | Amount of eluted Bi [ppm] | Less than 1 | 1.1 |
| | | Amount of eluted Pt [ppm] | Less than 1 | Less than 1 |
| | | Yield of ether carboxylate [%] | 87 | — |

TABLE 2

| | | | Example 2 | Comparative Example 2 |
|---|---|---|---|---|
| Step 1 | Liquid A: Pt/C catalyst aqueous dispersion | Pt amount in Pt/C catalyst [%] | 5 | 5 |
| | | Amount of fed catalyst [g] | 40 | 40 |
| | | Amount of fed water [mL] | 500 | 500 |
| Step 2 | Liquid B: Bi acidic solution | Bi in 2% AcOH aqueous solution [M] | 0.001 | 0.001 |
| | | Amount of fed 2% AcOH aqueous solution [mL] | 808 | 808 |
| | | pH at 20° C. | 3 | 3 |
| Step 3 | | Liquid to be dropped | Liquid A | Liquid B |
| Step 3' | | Dropping rate of liquid to be dropped [mL/min.] | 3.4 | 3.4 |
| | | Period for dropping [h] | 2.5 | 4 |
| | | Liquid receiving the dropping | Liquid B | Liquid A |
| | | Amount of AcOH to be added to liquid receiving the dropping [mL] | 2 | 2 |
| | | Temperature of liquid receiving the dropping [° C.] | 20 | 20 |
| | | Water content in catalyst [%] | 43.9 | 34.3 |
| Effects | | Amount of eluted Bi [ppm] | 13 | 28 |
| | | Amount of eluted Pt [ppm] | Less than 1 | 2 |
| | | Yield of ether carboxylate [%] | 74 | — |

Examples 3 to 5

Catalysts for these examples were obtained by conducting the same steps as in Example 1 except that conditions were changed to those described in Table 3, respectively. Further, the same method as in Example 1 was used to produce ether carboxylate, and the amount of metal elution from a catalyst and the yield of ether carboxylate were measured. Measured results are shown in Table 3.

Example 6

A catalyst was prepared by conducting the same steps as in Example 1. Further, the same method as in Example 1 was used to produce ether carboxylate except that the reaction time was 14 hours, and the amount of metal elution from the catalyst and the yield of ether carboxylate were measured. Measured results are shown in Table 3. The amount of metal elution was measured in the same manner as in Example 1 except for the following (1) and (2).
(1) In (1) of the preparation of sample solution for Example 1, a ceramic crucible was used to heat and dissolve a sample with an acid, but instead of that, a special closed vessel was used to treat a sample with an acid by a microwave method.
(2) In ICP measurement, an ICP mass spectrometer ELAN DRC II manufactured by PerkinElmer, Inc. was used.

It is considered that when Bi is carried on Pt, Bi receives electrons from adjacent Pt, so that the binding energy is reduced. That is, it is considered that as Bi is carried evenly on Pt without cohesion of Bi, the peak top binding energy value is reduced.

As described above, the peak top binding energy value of the catalyst prepared in Example 1 is lower than that of the catalyst prepared in Comparative Example 1, and thus, it is speculated that Bi is carried evenly on Pt. Then, it is believed that as a result of Bi being evenly carried on Pt, the catalyst prepared in Example 1 has an enhanced activity and metal elution is prevented.

<XPS Measurement Method>

A sample for analysis was obtained by dispersing a catalyst on a double-sided carbon tape adhered to a copper plate. An apparatus and conditions used for analysis were as follows.

Apparatus and Measurement Conditions Used for Analysis
Apparatus: PHI Quantera SXM (ULVAC-PHI Inc.)
X-ray source: monochromatic AlKα 1486.6 eV, 25 W, 15 kV
Beam diameter: 100 μm
Measuring range: 500×500 μm$^2$
Pass energy: 280.0 eV (survey), 112.0 eV (narrow)
Step: 1.00 eV (Survey), 0.20 eV (narrow)
Electrification correction: Neutralizer and Ar$^+$ irradiation
Take off angle of photoelectron: 45°

TABLE 3

|  |  |  | Example 3 | Example 4 | Example 5 | Example 6 |
|---|---|---|---|---|---|---|
| Step 1 | Liquid A: Pt/C catalyst aqueous dispersion | Pt amount in Pt/C catalyst [%] | 10 | 10 | 10 | 10 |
|  |  | Amount of fed catalyst [g] | 50 | 50 | 50 | 50 |
|  |  | Amount of fed water [mL] | 625 | 625 | 625 | 625 |
| Step 2 | Liquid B: Bi acidic solution | Bi in 2% AcOH aqueous solution [M] | 0.001 | 0.002 | — | 0.001 |
|  |  | Amount of fed 2% AcOH aqueous solution [mL] | 1034 | 517 | — | 990 |
|  |  | Bi in 2% HNO$_3$ aqueous solution [M] | — | — | 0.001 | — |
|  |  | Amount of fed 2% HNO$_3$ aqueous solution [mL] | — | — | 1035 | — |
|  |  | pH at 20° C. | 2 | 2 | 2 | 3 |
| Step 3 |  | Liquid to be dropped | Liquid A | Liquid A | Liquid A | Liquid A |
| Step 3' |  | Dropping rate of liquid to be dropped [mL/min.] | 3.4 | 3.4 | 3.4 | 3.4 |
|  |  | Period for dropping [h] | 3.1 | 3.1 | 3.1 | 3.1 |
|  |  | Liquid receiving the dropping | Liquid B | Liquid B | Liquid B | Liquid B |
|  |  | Amount of AcOH to be added to liquid receiving the dropping [mL] | 2.5 | 2.5 | 2.5 | 2.5 |
|  |  | Temperature of liquid receiving the dropping [° C.] | 40 | 20 | 20 | 20 |
|  |  | Water content in catalyst [%] | 56.8 | 45.19 | 20 | 57 |
| Effects |  | Amount of eluted Bi [ppm] | Less than 1 | 15 | Less than 1 | Less than 0.05 |
|  |  | Amount of eluted Pt [ppm] | Less than 1 | 12 | Less than 1 | 0.52 |
|  |  | Yield of ether carboxylate [%] | 84 | 87 | 81 | 95 |

Example 7

The catalyst produced in Example 1 was used and XPS (X-ray Photoelectron Spectroscopy) measurement was conducted by the following method. A result thereof is shown in The FIGURE.

The peak top binding energy value in the binding energy range between 162 and 155 eV was 157.8 eV.

Comparative Example 3

XPS measurement was conducted in the same manner as in Example 7 except that the catalyst produced in Comparative Example 1 was used. A photoelectron spectrum of Bi4F orbital thereof is shown in The FIGURE.

The peak top binding energy value in the binding energy range between 162 and 155 eV was 158.7 eV.

Detected elements: C1s (5), O1s (10), Na1s (20), Pt4f (30), Bi4f (30)

Binding energy value was corrected with C1s 284.8 eV derived from CH of carbon.

The invention claimed is:

1. A method for preparing a catalyst, comprising the following Steps 1, 2 and 3,
    Step 1: preparing an aqueous dispersion of a catalyst carrying Pt on activated carbon;
    Step 2: preparing an aqueous solution containing Bi in an ionic state; and
    Step 3: adding the aqueous dispersion obtained in Step 1 to the aqueous solution obtained in Step 2.

2. The method for preparing a catalyst according to claim 1, wherein Step 3 is conducted under a reducing atmosphere.

3. The method for preparing a catalyst according to claim 1, wherein the aqueous solution obtained in Step 2 contains an acid.

4. The method for preparing a catalyst according to claim 3, wherein the acid is one selected from acetic acid and nitric acid.

5. The method for preparing a catalyst according to claim 1, wherein the addition in Step 3 is conducted by continuous addition or divided addition.

6. The method for preparing a catalyst according to claim 1, wherein the Bi aqueous solution receiving the addition in Step 3 has a temperature of from 10° C. to 60° C.

7. The method for preparing a catalyst according to claim 1, wherein, in Step 3, the addition of the aqueous dispersion of the catalyst carrying Pt on activated carbon is conducted at a rate of from 1 mL/min. to 10 mL/min.

8. The method for preparing a catalyst according to claim 1, wherein, in Step 3, a time period required for the addition is from 15 minutes to 10 hours.

9. The method for preparing a catalyst according to claim 1, wherein the aqueous dispersion has a concentration of the catalyst carrying Pt on activated carbon of from 4% by mass to 12% by mass.

10. The method for preparing a catalyst according to claim 3, wherein the acid to be used is present in the Bi aqueous solution in an amount of from 1% by mass to 5% by mass.

11. The method for preparing a catalyst according to claim 1, wherein Bi is blended in the Bi aqueous solution in an amount of from 0.0001 M to 0.1 M.

12. The method for preparing a catalyst according to claim 1, wherein an ion source for Bi ion is at least one selected from bismuth nitrate pentahydrate, bismuth oxide, bismuth carbonate, and bismuth hydroxide.

13. A catalyst obtained by the preparation method according to claim 1.

14. A catalyst according to claim 13, wherein, in a photoelectron spectrum of a Bi4f orbital measured by XPS, a peak top binding energy value in a binding energy range between 162 and 155 eV is 158.5 eV or lower and 157.0 eV or higher.

15. A method for preparing an oxide of alcohol or an oxide of polyoxyalkylene alkyl ether, comprising: feeding, in the presence of the catalyst according to claim 13, oxygen to a composition containing alcohol or polyoxyalkylene alkyl ether, and water; and oxidizing by dehydrogenation the alcohol or the polyoxyalkylene alkyl ether.

16. The method for producing an oxide according to claim 15, wherein the alcohol or the polyoxyalkylene alkyl ether is one, or two or more kinds represented by the following general formula (1) or general formula (2), $$R^1O-H \tag{1}$$

in the general formula (1), $R^1$ is an aliphatic hydrocarbon group having a carbon number of from 2 to 40, $$R^2O\text{-}(AO)_n-H \tag{2}$$

in the general formula (2), $R^2$ is a hydrocarbon group having a carbon number of from 2 to 40; AO denotes an alkyleneoxy group having a carbon number of from 2 to 4; and n denotes a number of moles added of the alkyleneoxy group and is an integer of from 1 to 30.

* * * * *